(12) United States Patent
Howard et al.

(10) Patent No.: US 10,690,646 B2
(45) Date of Patent: Jun. 23, 2020

(54) UNDERWATER CAMERA AND WATER QUALITY MONITORING SYSTEM

(71) Applicants: Madison Mckensi Howard, Stockbridge, MI (US); Robert Lee Richards, Stockbridge, MI (US); Colin James Lilley, Stockbridge, MI (US); Faith Danielle Whitt, Stockbridge, MI (US); Sylvia Rebecca Whitt, Stockbridge, MI (US); Chelsey Ann Asquith, Stockbridge, MI (US); Hailey Ryanne Howard, Stockbridge, MI (US); Kael Allen Bunce, Stockbridge, MI (US); Julia Rose Marhofer, Stockridge, MI (US); Kelly Renee Cool, Stockbridge, MI (US); Lauren Lee Morris, Stockbridge, MI (US); Jillian Raye Cadieux, Stockbridge, MI (US); Michelle Elizabeth Zemke, Stockbridge, MI (US); Katelyn Marie Knieper, Stockbridge, MI (US); Baylee Ruthann Heidrich, Stockbridge, MI (US); Hailee Alesandra Fraser-Gutting, Stockbridge, MI (US)

(72) Inventors: Madison Mckensi Howard, Stockbridge, MI (US); Robert Lee Richards, Stockbridge, MI (US); Colin James Lilley, Stockbridge, MI (US); Faith Danielle Whitt, Stockbridge, MI (US); Sylvia Rebecca Whitt, Stockbridge, MI (US); Chelsey Ann Asquith, Stockbridge, MI (US); Hailey Ryanne Howard, Stockbridge, MI (US); Kael Allen Bunce, Stockbridge, MI (US); Julia Rose Marhofer, Stockridge, MI (US); Kelly Renee Cool, Stockbridge, MI (US); Lauren Lee Morris, Stockbridge, MI (US); Jillian Raye Cadieux, Stockbridge, MI (US); Michelle Elizabeth Zemke, Stockbridge, MI (US); Katelyn Marie Knieper, Stockbridge, MI (US); Baylee Ruthann Heidrich, Stockbridge, MI (US); Hailee Alesandra Fraser-Gutting, Stockbridge, MI (US)

(*) Notice: Subject to any disclaimer, the term of this patent is extended or adjusted under 35 U.S.C. 154(b) by 59 days.

(21) Appl. No.: 15/829,474

(22) Filed: Dec. 1, 2017

(65) Prior Publication Data
US 2019/0170720 A1     Jun. 6, 2019

(51) Int. Cl.
*G01N 33/18*      (2006.01)
*H04N 5/225*      (2006.01)
(Continued)

(52) U.S. Cl.
CPC ......... *G01N 33/18* (2013.01); *G01N 33/1886* (2013.01); *G03B 17/08* (2013.01);
(Continued)

(58) Field of Classification Search
CPC ...... G01N 33/18; G03B 17/08; G06K 9/6256; H04N 5/2252
(Continued)

(56) References Cited

U.S. PATENT DOCUMENTS

| | | | |
|---|---|---|---|
| 2010/0274491 A1* | 10/2010 | Andersen | E21B 43/0122 702/13 |
| 2014/0151308 A1* | 6/2014 | Kelly | C02F 1/50 210/739 |
| 2017/0137098 A1* | 5/2017 | Valsvik | B63G 8/39 |

* cited by examiner

*Primary Examiner* — On S Mung

(57) ABSTRACT

An underwater camera and water quality monitoring system provides the capability of shooting video or time lapse (Continued)

photography together with recording water condition or quality measurements in an integrated device for stationary, submerged deployment in a body of water under study. The underwater camera and water quality monitoring system has a configurable delay from submerged deployment in the waterway until image/video recording and water quality measurement sampling begins, allowing aquatic life activity to resume in the vicinity after disruption of the system deployment. The monitoring device may be used in combination with recognition software utilizing artificial intelligence techniques to identify species or individuals observed during monitoring.

9 Claims, 3 Drawing Sheets

(51) Int. Cl.
*G03B 17/08* (2006.01)
*G06K 9/62* (2006.01)
*G06K 9/20* (2006.01)
*G06K 9/00* (2006.01)

(52) U.S. Cl.
CPC ........... *G06K 9/209* (2013.01); *G06K 9/6256* (2013.01); *H04N 5/2252* (2013.01); *H04N 5/22521* (2018.08); *G06K 9/00* (2013.01)

(58) Field of Classification Search
USPC .......................................... 348/81
See application file for complete search history.

UNDERWATER CAMERA AND WATER QUALITY MONITORING SYSTEM

BACKGROUND

The natural ecology of many aquatic environments around the world is under threat due to human activity, climate change, and other sources. For example, invasive species have been spread and introduced into river, lake, and coastal systems, often unintentionally carried from other parts of the world by people traveling or in ballast water of ships, disrupting the natural habitat of aquatic life in these environments. Climate change or industrial pollutions also can disrupt aquatic life. To address these threats, there is a need to study aquatic life in these environments.

One example of a threatened system is the St. Clair River, which connects Lake Huron and Lake St. Clair in the Great Lakes Waterway of central North America. The native aquatic life and habitat of the St. Clair River is threatened by sea lamprey, an invasive species, which threat the Great Lakes Fisheries Commission is attempting to manage via application of lampricides. Sea lamprey larvae grow into parasitic marine animals who attach onto and kill native Great Lakes fish. Sea lamprey are each capable of killing as much as 40 pounds of fish during their 18 month lifespan. However, it is suspected that sea lamprey may evade the applications of lampricide, and the effectiveness of the lampricide on young lamprey may vary under different water conditions (e.g., temperature and pH).

Another example of a threatened aquatic life is fish whose spawning activity may be affected by change in water temperature, pH and other conditions due to climate change or nearby industrial activity. Tourist activity and water transportation also can pressure various species of aquatic life impacting aquatic ecosystems. Some other examples of aquatic life activity to investigate therefore include manta ray migration patterns in oceans, the spawning activity of lake trout, and invasive lion fish in coral reef ecosystems.

For the above and other purposes, the ability to study activities of aquatic species and how they may be affected in differing conditions of their water environment is needed. However, existing devices and systems for study of aquatic life have not been fully effective. For example, due to their movement and vibration, underwater drones can frighten away the aquatic species under study, making it difficult to observe their natural activity.

Therefore, there exists ample opportunity for improvement in technologies related to study of aquatic life and their environment.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Technologies are described for contemporaneous monitoring water quality and aquatic life activity, such as for investigating ways that water conditions impact aquatic life. In one example, an underwater camera and water quality monitoring system provides the capability of shooting video or time lapse photography together with recording water condition or quality measurements. For example, the underwater camera may record video or time lapse photography data to observe activities of interest of an aquatic species under investigation, and collect sampled pH and temperature readings over a monitoring or observation period.

In some implementations, the underwater camera and water quality monitoring system has a configurable delay from submerged deployment in the waterway until image/video recording and water quality measurement sampling begins. This delay may be configured to a suitable period of time that allows aquatic life activity to resume in the vicinity after disruption by the system deployment.

In one embodiment, the monitoring device may be used in combination with a species recognition or even an individual recognition software utilizing artificial intelligence techniques to identify species or individuals observed during the monitoring period.

As described herein, a variety of other features and advantages can be incorporated into the technologies as desired.

BRIEF DESCRIPTION OF THE DRAWINGS

For a better understanding of the present technology, and to show how embodiments of the same may be carried into effect, reference is made by way of example only to the following figures in which.

DETAILED DESCRIPTION

Figure 1:
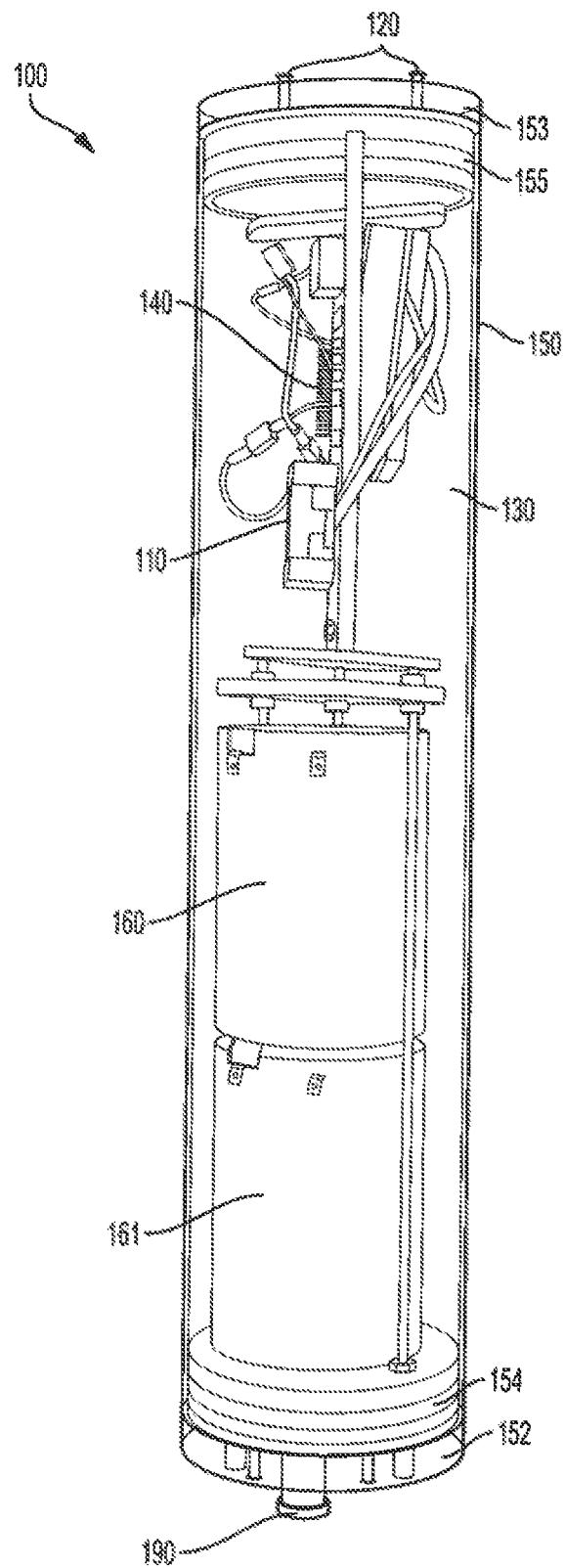
FIG. 1 is a front view of an example embodiment of an underwater camera and water quality monitoring system according to the invention.

As described herein and illustrated in FIG. 1, an underwater camera and water quality monitoring system 100 provides the capability to investigate aquatic life activities in relation to their environmental conditions. The system 100 has an camera module 110 and water quality sensors 120 housed together as an integrated system within a watertight sealed housing 130, which enables submersion under water and deployment into a water ecosystem. Using the camera module and water quality sensors, the system makes contemporaneous observation of the water conditions along with activity of aquatic life under investigation and records these observations for later retrieval and analysis.

In the illustrated example, the housing 130 is in the form of acrylic or plastic cylinder 150 and end caps 152-153 secured together with gaskets 154-155 and screw fasteners, which is water tight to a depth of 100 meters. In this example embodiment, the base consists of a clear acrylic cylindrical housing that is watertight. It has two acrylic Blue Robotics endcaps that have a tight seal. In these end caps, there are vent plugs 190 to release pressure when removing the end caps. In alternative designs, the housing may be in other solid shape or form, such as a sphere, cube or rectangular casing; and may be constructed of other materials such as metal (e.g., aluminum), glass, PVC, fiberglass, etc. The housing is most desirably transparent (at least in part) to allow a camera contained within the housing to observe activity in the exterior water environment in which the device is deployed.

The camera and sensors are powered by batteries 160-161, and operated by a control system 140 (shown in FIG. 3 and described in more detail below). In an illustrated example, the batteries are 12 V sealed batteries, which are connected to the control system via a voltage regulator that reduces the voltage to that suitable for powering the control system 140 (e.g., 5 V for the example Raspberry Pi and Arduino). The batteries 160-161 are desirably rechargeable for re-use of the system in multiple deployments and studies. The batteries are supported in place within the housing using a high density polyethylene plastic for cushioning and battery separator plates to reduce the chance of shifting during deployments.

Figure 2:
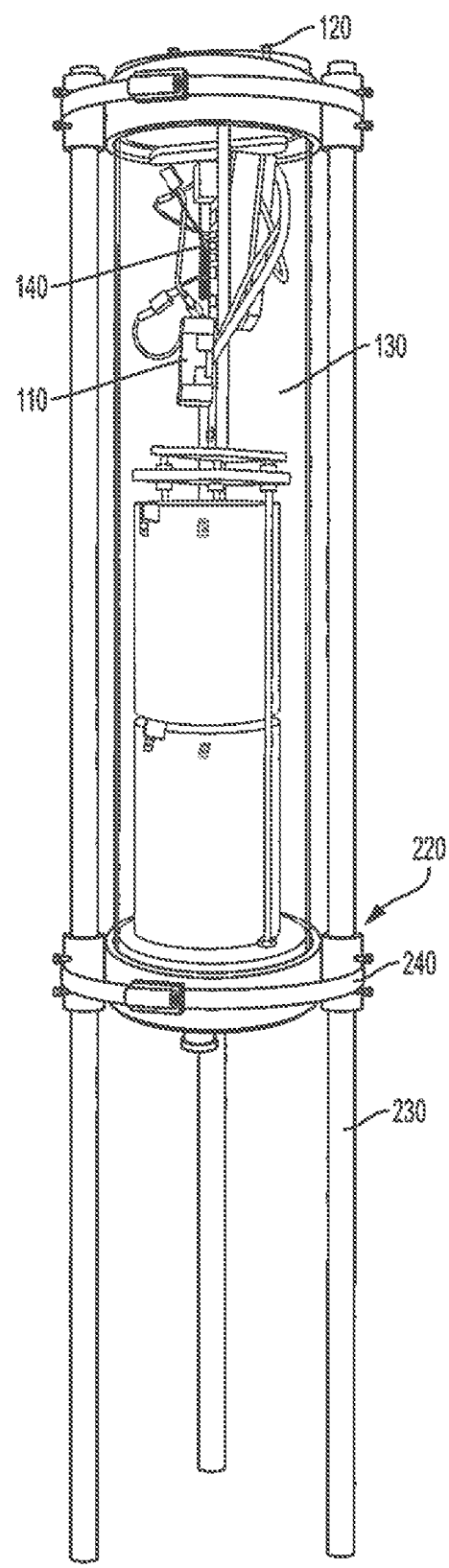
FIG. 2 is a view of the underwater camera and water quality monitoring system of FIG. 1 with a mounting system.

With reference now to FIG. 2, the system 100 has a mounting system 220 for mounting the housing to a variety of objects for submersion and deployment into a water ecosystem. For example, the mounting system 220 may attach the system to a landing frame or stand structure, such as to a set of iron rods serving as a tripod frame or to a cement block via straps or ties. The mounting system 220 most desirably weights the system for submersion and supports the system to stand upright on bottom of a body of water, so that the camera 110 and sensors 120 have a desired orientation and height above the floor or bed of the body of water for unobstructed observation.

During an investigation, the system 100 is transported to the body of water where the study is to take place. The system is then deployed by lowering from a boat, or manual placement by a diver or a wading technician (for shallower bodies of water). A floating marker, an electronic beacon or like may be attached to the system 100 to aid in retrieval of the system 100 at the end of the deployment.

Figure 3:
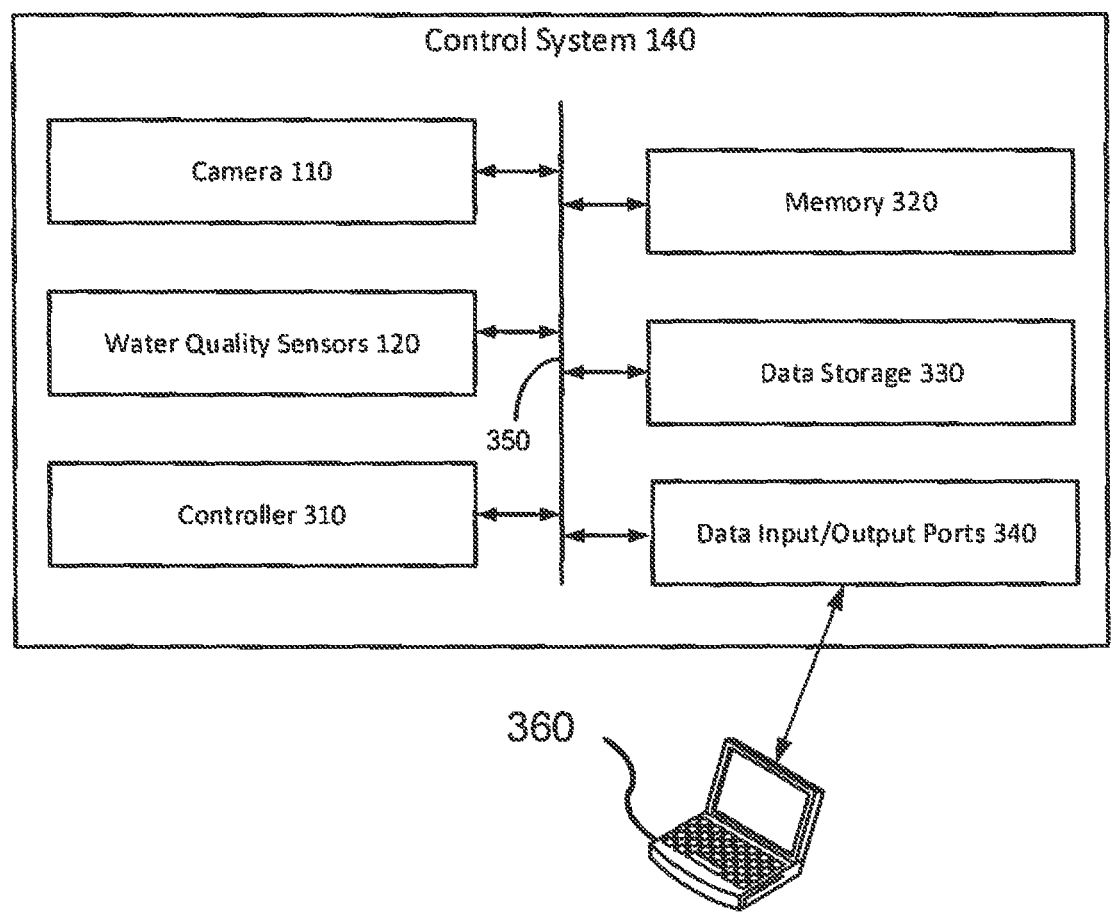
FIG. 3 is a schematic block diagram of a control system of the underwater camera and water quality monitoring system of FIG. 1.

FIG. 3 illustrates electronic components of the control system 140 for the underwater camera and water quality monitoring system 100. The camera module 110 and water quality sensors 120 operate under control of a controller 310 and programming stored in a memory 320. The controller 310 and memory 320 may be a microcontroller, such as an Arduino single board microcontroller which is an open source microcontroller kit available from various suppliers. The Arduino microcontroller includes on board SRAM memory. Alternatively, other microcontrollers or microprocessors may be used as the controller 310.

The control system further includes a data storage 330 and data input/output ports 340. The data storage 330 records data during deployment of the system 100 in a body of water. The data storage is desirably a solid state drive (SSD), but other data storage components alternatively may be used such as disk or tape drive, flash memory, RAM and other type storage. The data storage preferably has a storage capacity adequate to record data produced from the camera 110 and sensors 120 over its deployment period. In one example, the data storage may be a 1 terabyte PiDrive, which is adequate to record data from the camera and sensors for at least a 24 hour observation period. Other data capacities may be used as may be suitable to the desired deployment period, storage format, etc.

In accordance with its programming, the controller controls the camera module 110 to capture time lapse photography and/or video, and records the camera data in data storage 330. The camera module 110 may be a single camera or a set of cameras with various imaging capabilities. One example camera is capable of imaging visible light. In other examples, the camera may additionally be capable of imaging other light spectrum, such as the infrared spectra (for night vision photography); stereo imaging; depth sensing; and other types of photography. The camera may include a light source to enable imaging during low light or night conditions. In one example, the camera module is a Raspberry Pi camera module. Alternative implementations may instead have a Go Pro camera or that of various other vendors.

The controller also controls taking of measurements by the water quality sensors 120, and records the measurements data in the data storage 330. The water quality monitoring sensor 120 includes sensors that can collect temperature and pH readings. The sensors may additionally include other sensor(s) used to measure other attributes, e.g., dissolved oxygen, salinity, conductivity, resistivity, oxygen reduction potential, depth, pressure, etc. In an illustrated example, the sensors are made up of an Atlas Scientific sensor package. Suitable water quality sensors are available from various other suppliers. The controller logs these readings into the data storage 330.

The controller may provide a variety of operating modes. In one example, the controller is programmed to operate after deployment into the body of water under study with a delay period before an observation period. In particular, the system is powered on and the operating mode activated at deployment (such as, just before lowering the system into place on a bed of a river, lake or ocean). Upon activation, the controller begins timing a delay period, such as 24 hours or other desired delay. Because the deployment of the system into the body of water may disrupt the normal activity of aquatic life in the vicinity, this delay period allows time for activity of the aquatic life that is to be subject of study to return to normal activity before observation begins. After expiration of the delay period, the controller then causes the camera and sensors to start their operation (i.e., capturing images/video, and obtaining water quality measurement samples) and log the data acquired by the camera and sensors to the data storage 330.

During the observation period, the controller causes data from the camera 110 to be recorded to the data storage 330. In an illustrated example, the controller causes the camera to record video over a 24-hour observation period. The controller and camera may split the video into smaller interval segments (e.g., 10-minute segments) for ease of access and viewing. Alternatively, the controller and camera can shoot time lapse photography over the observation period and record to the data storage. The recorded data can be in any video or image format, such as MPEG, H.264, JPEG, etc.

The controller also causes measurements from the water quality sensors 120 to be recorded in the data storage 330 during the observation period. In an illustrated example, the controller and sensors collect temperature and pH readings at 30-minute sampling intervals and writes the data to the data storage. The sensor data may be logged as a .CSV format file, or other format that may be convenient for later off load and retrieval.

At the conclusion of the observation period, the controller may shut down operation of the camera and sensors and conclude the recording of data to the data storage.

The controller may be programmable such as to vary the durations of the delay period and observation period, as well as frequency of water quality measurement sampling and time lapse photography. For example, shorter or longer delay periods may be programmed. Further, the observation period may be shorter or longer up to the available capacity of the data storage for recording the recording formats.

The control system also may provide other operating modes. As one example, the control system may omit a delay period, and begin recording camera and sensor data immediately for an observation period. In another example, the control system may operate under certain light conditions or certain times of day. For example, the control system may cause the camera and water quality sensors to operate during daylight while natural visible light photography can be recorded. As another example, the control system may cause camera operating in infrared spectrum and water quality sensing to operate and record data at night to capture activity of nocturnal aquatic life. In other examples, the control system may cycle between delay and observation periods to allow observation over extended lengthy study periods (e.g., weeks or months).

After retrieval of the system 100 from the body of water under study at the end of the deployment, the recorded data is off-loaded from the control system 140 to a computer 360 (e.g., a laptop or desktop personal computer). The control system includes data input/output ports 340, such as a USB connector, for connecting with the computer 360. This allows transfer of the data logged from the camera 110 and water quality sensors 120 to the computer 360. The computer may include software such as a media viewer for video play back and photo viewing, and spreadsheet or other data visualization or analysis software to produce graphs, charts, spread sheets or other data viewing formats.

For analysis of the camera data, the computer 360 may run image/object recognition software based on machine learning technology, such as deep learning and deep neural network, which has been trained to recognize particular aquatic life genus, species or even individuals. For example, the system 100 may be used in a study to track the activity of manta rays, ocean mammals (e.g., whales or dolphins) or other aquatic life. In the manta ray study, for example, the machine learning classifier is trained on a training set of images of individual of the manta rays. The trained classifier may then be used to analyze the camera data collected from the system to identify activity of individual manta rays during the study. In other examples, a classifier may be trained via machine learning to recognize a species or plural species of interest (e.g., trout or salmon at a spawning area). The classifier can then process the camera data to produce a count of a number of such species identified in the camera data, or a duration during which such species appears in the camera data.

In some embodiments of the system 100, recognition software incorporating a machine learning classifier trained to recognize a genus, variety, species or individuals of aquatic life under study can be included in the control system 140. The recognition software can then be used to control the operation of the system 100. For example, the controller 310 use the recognition software to recognize the particular genus, variety, species or individual is currently within camera view, and if so control logging or recording of the camera data and water quality data to the data storage 330 conditioned on recognized aquatic life being present.

Depending on study scope, an investigation may involve deploying a single one of the underwater camera and water quality monitoring system 100 or multiple such systems over a study area. One example study is that of investigating the influence of water quality on the effectiveness of lampricide use in managing the invasive sea lamprey in the St. Clair River in the North American Great Lakes region. It has long been known that the toxicity of the lampricide 3-trifluoromethyl-4-nitrophenol (TFM) is influenced by chemical and physical properties of water. As the pH, conductivity, and alkalinity of water increase, greater concentrations of TFM are required to kill sea lamprey (*Petromyzon marinus*) larvae. Consequently, the concentration of TFM required for effective treatment may be expected to vary among streams.

For this study example, multiple of the underwater camera and water quality monitoring systems 100 configured with different operating modes may be used. For example, the study may consist of deploying 16 of the systems, spanning both sides of the middle channel of the St Clair River. For this study, the systems are programmed with a 24-hour delay after deployment to the environment. Eight of the systems are configured to record video and the other eight configured for time-lapse photography, both over an observation period of five hours. The water quality monitoring sensors of the systems take pH and temperature readings every thirty minutes for the duration of the study Terminology The terms "system" and "device" are used interchangeably herein. Unless the context clearly indicates otherwise, neither term implies any limitation on a type of control system or computing device. In general, a controller may include any combination of special-purpose hardware and/or general-purpose hardware with software implementing the functionality described herein.

For the sake of presentation, the detailed description uses terms like "determine" and "use" to describe operations in a electronic control system. These terms are high-level abstractions for operations performed by a microcontroller, and should not be confused with acts performed by a human being. The actual device operations corresponding to these terms vary depending on implementation.

Although the operations of the described systems are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

The above described systems should not be construed as limiting in any way. Instead, the present disclosure is directed toward all novel and nonobvious features and aspects of the various disclosed embodiments, alone and in various combinations and sub combinations with one another. The disclosed methods, apparatus, and systems are not limited to any specific aspect or feature or combination thereof, nor do the disclosed embodiments require that any one or more specific advantages be present or problems be solved.

The technologies from any example can be combined with the technologies described in any one or more of the other examples. In view of the many possible embodiments to which the principles of the disclosed technology may be applied, it should be recognized that the illustrated embodiments are examples of the disclosed technology and should not be taken as a limitation on the scope of the disclosed technology.

What is claimed is:
1. A water quality monitoring and image capture device for submersive deployment in a body of water, comprising:
   a water tight sealed housing;
   a camera module disposed within the sealed housing;
   one or more water quality monitoring sensors;
   a data logger communicatively coupled to the camera and the one or more water quality monitoring sensors, the data logger_ operating to record measurement data from the one or more water quality monitoring sensors and camera data from the camera module;

control electronics operating to cause the data logger to record the measurement data and the camera data over an observation period commencing after a delay period from activation at submerged deployment of the device in the body of water;

wherein the water quality monitoring and image capturing device further comprising a mounting system attached to a weighted landing frame for standing on a bottom of a body of water, the weighted landing frame enabling the mounting system to stand upright on the bottom of the body of water wherein the camera module and the one or more water quality monitoring sensors have a desired orientation and a height above the bottom of the body of water for unobstructed observation.

2. The device of claim 1 wherein the control electronics have configurable duration of delay and observation periods.

3. The device of claim 1 wherein the one or more water quality monitoring sensors comprise a pH sensor and a depth sensor.

4. The device of claim 1 wherein the one or more water quality monitoring sensors comprise at least one of a pH sensor, a pressure sensor, a depth sensor, a conductivity sensor, and a resistivity sensor.

5. The device of claim 1 wherein the camera data is time lapse photography.

6. The device of claim 1 wherein the camera data is video.

7. The device of claim 1 further comprising the control electronics having a machine learning based recognition capability operative to recognize presence of at least one of a genus, variety, species or individual of aquatic life in the camera data, and cause the data logger-to record the measurement data and the camera data based on the recognized presence.

8. The device of claim 1, wherein the weighted landing frame comprises a set of iron rods serving as a tripod frame.

9. The device of claim 1, wherein the weighted landing frame comprises an attached cement block.

* * * * *